United States Patent [19]

Kressirer

[11] Patent Number: 5,365,798
[45] Date of Patent: Nov. 22, 1994

[54] PIPETTING DEVICE

[75] Inventor: Rudolf Kressirer, Kelkheim/Ts, Germany

[73] Assignee: Behringwerke Aktiengesellschaft, Marburg/Lahn, Germany

[21] Appl. No.: 60,570

[22] Filed: May 13, 1993

[30] Foreign Application Priority Data

May 15, 1992 [DE] Germany .............................. 4216128

[51] Int. Cl.⁵ .............................................. G01N 1/14
[52] U.S. Cl. .................... 73/864.11; 73/863.11; 366/140
[58] Field of Search ............ 73/863.11, 864.01, 864.11; 366/108, 117, 118, 120, 123, 128, 140, 148, 167, 276, 277, 278, 243; 422/100

[56] References Cited

U.S. PATENT DOCUMENTS

| | | | |
|---|---|---|---|
| 3,182,970 | 5/1965 | Ivanoff | 366/278 |
| 3,780,992 | 12/1973 | Nishi et al. | 366/116 |
| 4,874,114 | 10/1989 | Guigan | 73/864.11 |
| 5,178,019 | 1/1993 | Keiter | 73/863.11 |

FOREIGN PATENT DOCUMENTS

| | | |
|---|---|---|
| 0316698A1 | 5/1989 | European Pat. Off. . |
| 0463468A1 | 1/1992 | European Pat. Off. . |
| 9111441 | 2/1992 | Germany . |
| 62-179380 | 8/1987 | Japan . |

*Primary Examiner*—Robert Raevis
*Attorney, Agent, or Firm*—Finnegan, Henderson, Farabow, Garrett & Dunner

[57] ABSTRACT

In the pipetting device for mixing liquids, a pipetting tube (7) is located in a receiving arrangement (6), and the receiving arrangement (6) is rotatably (10) mounted in a mounting device (5) and connected via a coupling (12, 13) to an eccentric drive (26).

7 Claims, 2 Drawing Sheets

PIPETTING DEVICE

DESCRIPTION

The invention relates to a pipetting device for mixing liquids.

For quantitative protein determination in body fluids such as, for example, serum, urine or spinal fluid, the latter are diluted where appropriate and mixed with reagent (antiserum) in a defined ratio by volume, and the turbidity occurring owing to the reaction is measured. The liquids are manipulated with pipetting devices and mixed with a separate stirrer. The disadvantages connected with this are the additional space required for the stirrer, and the additional cross-contamination with sample material, which influences the accuracy of the results measured in sensitive assays. A further disadvantage is the additional heat introduced by the stirrer, which interferes with keeping the reaction temperature constant and thus likewise influences the accuracy of the results measured.

SUMMARY OF THE INVENTION

The intention of the invention is to remedy this. The invention achieves the object by a pipetting device in which a pipetting tube is located in a receiving arrangement, and the receiving arrangement is rotatably mounted in a mounting device and connected via a coupling to an eccentric drive.

The coupling can comprise two pressure rollers and the eccentric drive can comprise an eccentric arranged on the shaft of a motor. The eccentric with motor can be arranged on the mounting device for the receiving arrangement. The pipetting tube can be provided with a heating arrangement and be divided into two zones, where the first zone contains the pipetting tip which has a relatively small pipetting volume, and the second zone connected thereto has a larger pipetting volume than the first zone. The pipetting tube can be straight in the first zone and be coiled and in contact with a heat transfer means in the second zone. The pipetting tube can furthermore be provided with a coupling for a feedline which is located on the receiving arrangement.

The advantages of the invention are essentially to be regarded as the possibility of achieving metered volumes for the individual components as far as 2 $\mu$l with an accuracy of 1%, and mixing of the components.

BRIEF DESCRIPTION OF THE DRAWINGS

The invention is explained in detail hereinafter by means of an exemplary embodiment from which other important features are evident.

DETAILED DESCRIPTION OF THE PREFERRED EMBODIMENT

Figure 1:
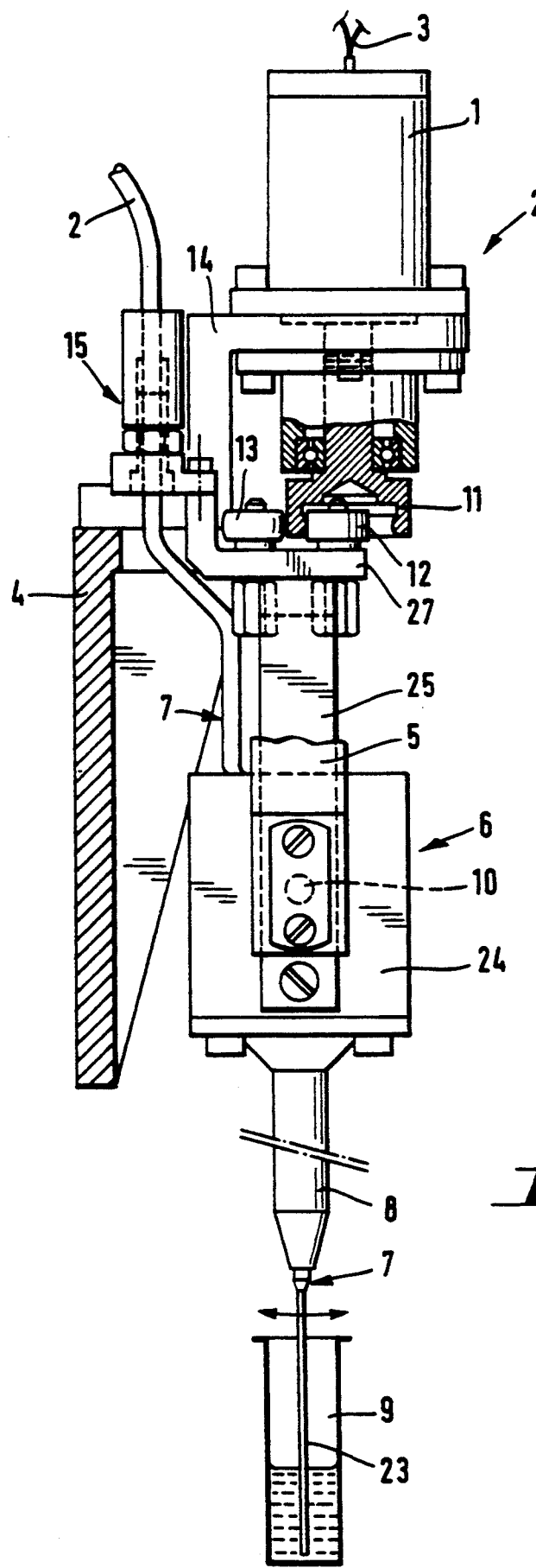
FIG. 1 shows the pipetting device from the front, partly in section.
Figure 2:
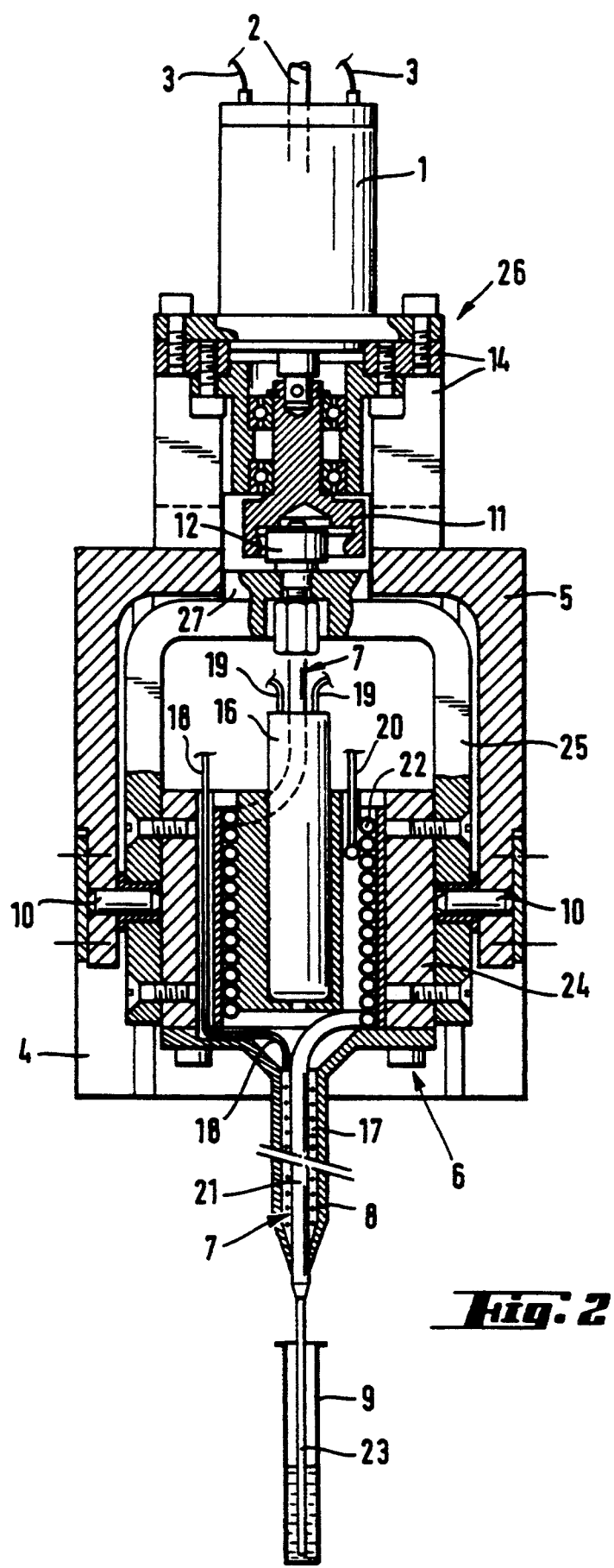
FIG. 2 shows the pipetting device from the side, partly in section.

The pipetting tube (7) is located in a receiving arrangement (6). The receiving arrangement (6) is composed of a U-shaped frame (25) and a casing (24). The frame (25) is rotatably mounted on a mounting device (5) via a link (10) and connected via a coupling, for example pressure rollers (12, 13), to an eccentric drive (26). The eccentric drive (26) is essentially composed of the eccentric (11) and the motor (1) with feedline (3). The eccentric drive (26) is located on the mounting device (5), and the mounting device (5) is provided with a support plate (4). The frame (25) is provided with a cross arm (27) which supports the pressure rollers (12, 13) and a coupling (15) which establishes the connection of the pipetting tube (7) to an elastic feedline (2). The pipetting tube (7) has a first zone (21) which is designed to be straight and supports the pipetting tip (23) with a relatively small pipetting volume, and has a second zone (22) which is connected thereto and is designed as a coil. The pipetting tube (7) is provided with a heating device (17) in the first zone (21) and with a heat transfer means, a heating cartridge (16), in the second zone. The heating devices (16, 17) can operate separately from one another. (8) indicates a supporting tube for the straight part (zone 21) of the pipetting tube (7), (18, 19) indicates the feedlines for the heating devices (16, 17), (14) indicates the mounting device for the motor (1), and (20) indicates a temperature sensor. The eccentric drive (26) causes the pipetting tube (7), as indicated by the arrow, to execute a backwards and forwards oscillating motion, which agitates, and thus mixes, the contents of the cuvette (9).

I claim:

1. A pipetting apparatus for mixing liquids, the apparatus comprising:
   a holder;
   a pipetting tube held by the holder;
   a mounting device rotatably mounting the holder; and
   an eccentric drive for causing the pipetting tube to oscillate and mix liquids, the eccentric drive being connected to the mounting device by a first coupling.

2. The apparatus as claimed in claim 1, wherein:
   the first coupling comprises first and second pressure rollers; and
   the eccentric drive comprises an eccentric fixed on a shaft of a motor.

3. The apparatus as claimed in claim 1, further comprising:
   a heating device for heating the pipetting tube, said tube having first and second zones, the first zone including a tip of the pipetting tube having a relatively small pipetting volume, and the second zone being coterminous with the first zone and including a portion of the pipetting tube having a pipetting volume larger than the pipetting volume in the first zone.

4. The apparatus as claimed in claim 3, wherein the pipetting tube is straight in the first zone and coiled in the second zone.

5. The apparatus as claimed in claim 3, wherein the pipetting tube is in contact with the heating device that further comprises a heat-conducting heat transfer means in a region of the second zone.

6. The apparatus as claimed in claim 1, further comprising:
   a second coupling mounted on the holder for connecting the pipetting tube to a feedline.

7. A pipetting apparatus for mixing liquids, the apparatus comprising:
   a holder;
   a pipetting tube held by the holder;
   a mounting device rotatably mounting the holder;
   an eccentric drive for causing the pipetting tube to oscillate and mix liquids and including an eccentric fixed on a shaft of a motor, the eccentric drive being connected to the mounting device by a first coupling having first and second pressure rollers; and
   a second coupling mounted on the holder for connecting the pipetting tube to a feedline.

* * * * *